United States Patent [19]

Bert

[11] E Re. 28,793

[45] Reissued May 4, 1976

[54] END ATTACHMENT FOR WATCH BAND AND SELF-CONTAINED COMPONENT FOR USE IN MAKING THE SAME

[75] Inventor: Stephen F. Bert, West Warwick, R.I.

[73] Assignee: Textron Inc., Providence, R.I.

[22] Filed: Aug. 18, 1975

[21] Appl. No.: 605,288

Related U.S. Patent Documents

Reissue of:

[64] Patent No.: 3,897,612
Issued: Aug. 5, 1975
Appl. No.: 491,141
Filed: July 25, 1974

[52] U.S. Cl. ..... 24/265 B; 224/4 E
[51] Int. Cl.[2] ..... A44C 5/18
[58] Field of Search ..... 224/4 D, 4 E; 24/73 WW, 24/265 WS, 265 B

[56] References Cited

UNITED STATES PATENTS

| | | | |
|---|---|---|---|
| 2,653,369 | 9/1953 | Rodriguez | 24/265 B |
| 2,713,445 | 7/1955 | Speck | 224/4 D |
| 3,675,284 | 7/1972 | Rieth | 24/265 B |
| 3,740,804 | 6/1973 | Levinger | 24/265 WS |

FOREIGN PATENTS OR APPLICATIONS

| | | | |
|---|---|---|---|
| 2,044,864 | 2/1971 | France | 24/265 B |
| 2,015,412 | 10/1971 | Germany | 24/265 B |

*Primary Examiner*—Donald A. Griffin

[57] ABSTRACT

An end attachment for watch bands which permits use of a watch band with wrist watches having different spacings between their attachment lugs. The end attachment includes a self-contained component which includes a generally tubular member, coiled compression spring means and a pair of generally tubular inserts which are slideable within the generally tubular member. One of the inserts has its inner end positioned against one outer end of said spring means, the other insert has its inner end positioned against another outer end of said spring means and stop means on the generally tubular member act upon the inserts to limit their outward sliding movements under the action of the spring means. The attachment also includes an ornamental top shell having a generally tubular portion attached about the generally tubular portion of the self-contained component and a member extending laterally therefrom with means for attaching the top shell to the end of a watch band. The top shell may be deeply impressed with the design of the links of the watch band to which the end attachment is to be attached without interfering with the sliding movements of the inserts within the generally tubular member of the self-contained component.

13 Claims, 8 Drawing Figures

END ATTACHMENT FOR WATCH BAND AND SELF-CONTAINED COMPONENT FOR USE IN MAKING THE SAME

Matter enclosed in heavy brackets [ ] appears in the original patent but forms no part of this reissue specification; matter printed in italics indicates the additions made by reissue.

BACKGROUND OF THE INVENTION

Wrist watch bands are often sold separate from the watches to which they are to be attached. One reason for this is that styles in watch bands change more rapidly than styles in watches and watch cases and, during the life of the watch, wearers therefore frequently use several different watch bands. Another reason is that the preference of the user for watch bands of different types such as plastic, metal, snake chain, buckle secured, or expansible may change from season to season or at the whim of the person concerned.

One problem presented to the manufacturer of watch bands sold separately from watches is that the watch case lugs between which the watch band end attachments are to be secured are not uniformly spaced in all watches. The watch band manufacturer therefore has been forced to make watch bands having a variety of widths of end attachments so as to fit various watch sizes or else the jeweler from whom the watch band is bought must perform delicate and time consuming operations on the end attachment to make it fit a particular watch. These tasks are expensive for the watch band manufacturer and for the retail dealer.

There have been many proposed solutions of the problem over a long period of time.

In one group of prior art patents the elements of the end attachment of the watch bands must be removed, and/or replaced, and/or filed by the retail jeweler to cause the end attachment to fit watches having different distances between the lugs. This is a troublesome and time consuming task for the retail jeweler. Such patents include the following U.S. patents:

| Patent No. | Date | Inventor |
|---|---|---|
| 1,836,772 | December 15, 1931 | Rossman |
| 2,883,727 | March 12, 1957 | Obst |
| 3,118,209 | January 21, 1964 | Vollet |
| 3,675,284 | July 11, 1972 | Rieth |
| 3,678,544 | July 25, 1972 | Bert |

In another group of prior art patents the part of the end connector which directly encircles the slideable width adjusting elements cannot be impressed with deep designs to match the design of the links of the watch band without interfering with slideability of the width adjusting elements. Such patents include the following U.S. patents:

| Patent No. | Date | Inventor |
|---|---|---|
| 1,713,533 | May 21, 1929 | Jones |
| 2,653,369 | September 25, 1953 | Rodrigues |
| 3,160,938 | December 15, 1964 | Minutoli |
| 3,477,107 | November 11, 1969 | Nadeau |
| 3,705,456 | December 12, 1972 | Bruner |
| 3,740,804 | June 26, 1973 | Levinger |

While patent to Fachon U.S. Pat. No. 2,775,861 recognizes the desirability of providing a continuation of the design of the links of the watch band to the end connector it solves the problem by providing a separate filler member between the spring bar and the watch case and the spring bar interrupts the continuity of the design. Furthermore in this patent no means are provided for adjusting the width of the end connector to fit between differently spaced lugs of watch bands.

In a still further group of patents spring actuated members are provided for automatically adjusting the width of the end connector to fit between differently spaced lugs of watches but the end connectors are very expensive to manufacture and are incapable of using self-contained generally tubular components which can be automatically assembled by machinery prior to assembling an ornamental top shell of the end connector to the self-contained component. Such patents include the following U.S. patents:

| Patent No. | Date | Inventor |
|---|---|---|
| 2,713,445 | July 19, 1955 | Speck |
| 2,807,855 | October 1, 1959 | Rodriguez |
| 3,217,374 | November 16, 1965 | Sang |
| 3,030,686 | April 24, 1962 | Burkhardt |
| 3,477,107 | November 11, 1969 | Nadeau |
| 3,707,744 | January 2, 1973 | Manzo |

From the foregoing prior art it is apparent that there has been a recognized long-felt need for an end attachment for watch bands for use in attaching a watch band between attachment lugs of wrist watch cases which is economical to manufacture and assemble, can be deeply impressed with the design of the links of the watch band, does not require the retail dealer to stock either watch bands having end attachments of different widths or additional replacement parts and can be quickly and easily adapted by the retailer to fit between the lugs of watches which are spaced different distances apart without removing and/or replacing and/or filing elements of the end connector.

BRIEF SUMMARY OF THE INVENTION

One object of this invention is to provide an end attachment for a watch band adapted to be mounted between lugs of wrist watch cases which are spaced different distances apart and which is economical to manufacture and assemble.

Another object is to provide such an end attachment in which an element of the end attachment can be provided with deeply impressed designs to match the designs of the links of the watch band without interfering with free slideability of the width adjusting elements.

A further object is to provide a self-contained component for making an end attachment for a watch band which comprises a generally tubular member, coiled compression springs and generally tubular inserts which can be assembled automatically.

Another object is to provide a new end attachment for a watch band.

Further objects and advantages of the invention will be apparent to persons skilled in the art from the following description taken in conjunction with the accompanying drawings.

In general, the end attachment of this invention includes a generally tubular member formed from a strip of metal, and coiled compression spring means within the tubular member. A pair of generally tubular inserts are provided which are adapted to slide within the generally tubular member. Each insert is formed from a strip of metal and has a generally rectangular slot formed between the edges of the strip. This slot has an open outer end and an inner end which is formed by the edges of a pair of tabs which extend inwardly towards each other from the adjacent ends of the strip. A pair of tabs is provided, one adjacent to one end of the strip from which the generally tubular member is formed and the other adjacent to its other end and the ends of these tabs extend into the rectangular slots respectively and engage the edges of the tabs of the inserts, thereby to stop outward movements of the inserts by the coiled springs.

The end attachment also includes an ornamental top shell which comprises a generally tubular portion surrounding at least the upper and end portions and part of the lower portion of the generally tubular member, means for securing the generally tubular portion of the top shell to the generally tubular member, and a member extending laterally from the generally tubular portion of the top shell which includes means for attaching it to the end of a watch band.

In the preferred embodiment the generally tubular member, the coiled compression spring means and pair of generally tubular inserts are formed as a self-contained component and the generally tubular portion of the ornamental top shell is applied to the exterior of the generally tubular member of the component.

In another preferred embodiment the ornamental top shell is impressed with the deeply impressed design of the links of the watch band to which the end attachment is to be attached and, because the generally tubular member is between the inserts and the top shell, the ornamental design impressed in the top shell does not interfere with the sliding movements of the inserts within the generally tubular member.

In a further preferred embodiment the generally tubular member comprises stop means substantially midway between its ends for engaging the coiled compression spring means.

In yet another preferred embodiment the coiled compression spring means comprises a pair of coiled compression springs, one extending outwardly from one side of the stop means and the other extending outwardly from the other side of the stop means.

In a still further embodiment the ends of the strip of metal from which the generally tubular member is formed comprises oppositely positioned cutout portions substantially intermediate its ends and the stop means comprises a tab extending from the side of one of these cutout portions thereby dividing the cutout portion into a pair of cutout portions. In this embodiment the means for securing the generally tubular portion of the top shell to the generally tubular member comprises a pair of spaced tabs which extend into this pair of cutout portions.

Preferably the tab adjacent to one end of the generally tubular member extends in one direction near one end of the strip of metal and the tab adjacent to the other end of the generally tubular member extends in the opposite direction near the other end of the strip of metal so the generally tubular member is symmetrical facilitating automatic assembly of the self-contained component.

The self-contained component for making the end attachment includes a generally tubular member formed from a strip of metal. A pair of tabs is provided, one adjacent to one end of the strip of metal and the other adjacent to the other end thereof, and the ends of these tabs are bendable towards the interior of the generally tubular member.

Coiled compression spring means is located within the generally tubular member.

A pair of generally tubular inserts are adapted to slide within the generally tubular member. Each insert is formed from a strip of metal and has a generally rectangular slot formed between the edges of the strip. This slot has an open outer end and an inner end which is formed by the edges of a pair of tabs which extend inwardly towards each other from the adjacent ends of the strip.

This self-contained component can be assembled by an automatic machine which inserts the coiled compression spring means into the generally tubular member then simultaneously inserts the inserts at opposite ends of the generally tubular member with the open ends of their rectangular slots pointing outwardly and moves them inwardly compressing the spring means until the inner ends of the rectangular slots pass beyond the tabs of the generally tubular member and then bends the ends of the tabs into the longitudinal slots, so that the inner edges of the tabs of the generally tubular member are adapted to engage the edges of the tabs which form the inner ends of the rectangular slots of the inserts when the inserts are moved outwardly predetermined distances by the springs, thereby to stop further outward movements of the inserts by the coiled springs.

In a preferred embodiment of the component the tab adjacent to one end of the generally tubular member extends in one direction near one end of the strip of metal and the tab adjacent to the other end of the generally tubular member extends in the opposite direction near the other end of the strip of metal.

In a further preferred embodiment the generally tubular member comprises stop means substantially midway between its ends for engaging the coiled compression spring means.

In yet another preferred embodiment the coiled compression spring means comprises a pair of coiled compression springs, one extending outwardly from one side of the stop means and the other extending outwardly from the other side of the stop means.

The stop means preferably comprises a bendable tab which extends from one end of the strip of metal substantially midway between its ends.

Preferably the ends of the strip of metal from which the generally tubular member is formed comprises oppositely positioned cutout portions substantially midway between their ends and the stop means comprises a tab extending from one side of one of the cutout portions substantially intermediate its ends thereby dividing the cutout portion into a pair of cutout portions.

It will be apparent to persons skilled in the art that this invention has solved the above described long-felt need and satisfied the above described objects.

DETAILED DESCRIPTION OF THE PREFERRED EMBODIMENT

The end attachment embodying this invention is adapted to be connected to any conventional wrist watch having two pairs of laterally spaced lugs.

Figure 1:
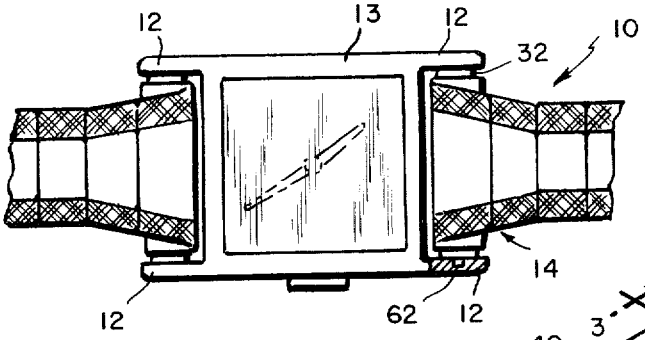
FIG. 1 is a top plan view showing two ends of a ladies' watch band with the end connectors in place between the lugs of a wrist watch.

Referring to FIG. 1, 10 designates an expansion watch band secured between the spaced lugs 12 of the watch 13 by the end attachment 14.

While the end attachment is adapted to be used with any conventional watch band, it is shown attached to an expansion watch band of the type shown in U.S. Pat. No. 3,307,348 to Vanover although the watch band shown in the present application uses only one spring in each link. Such a watch band comprises a row of top links 15 (FIGS. 2 and 3) and a row of bottom links 16, each link extending in a direction generally transverse to the length of the linkage. There is a leaf spring 17 located in each link and the links are held together by U-shaped connecting members 18 having their legs positioned between the ends of the springs and the outer walls of the top and bottom links respectively, thus to provide an expansible linkage. The watch band is completed by securing ornamental top shells 19 to the top links.

Figure 6:
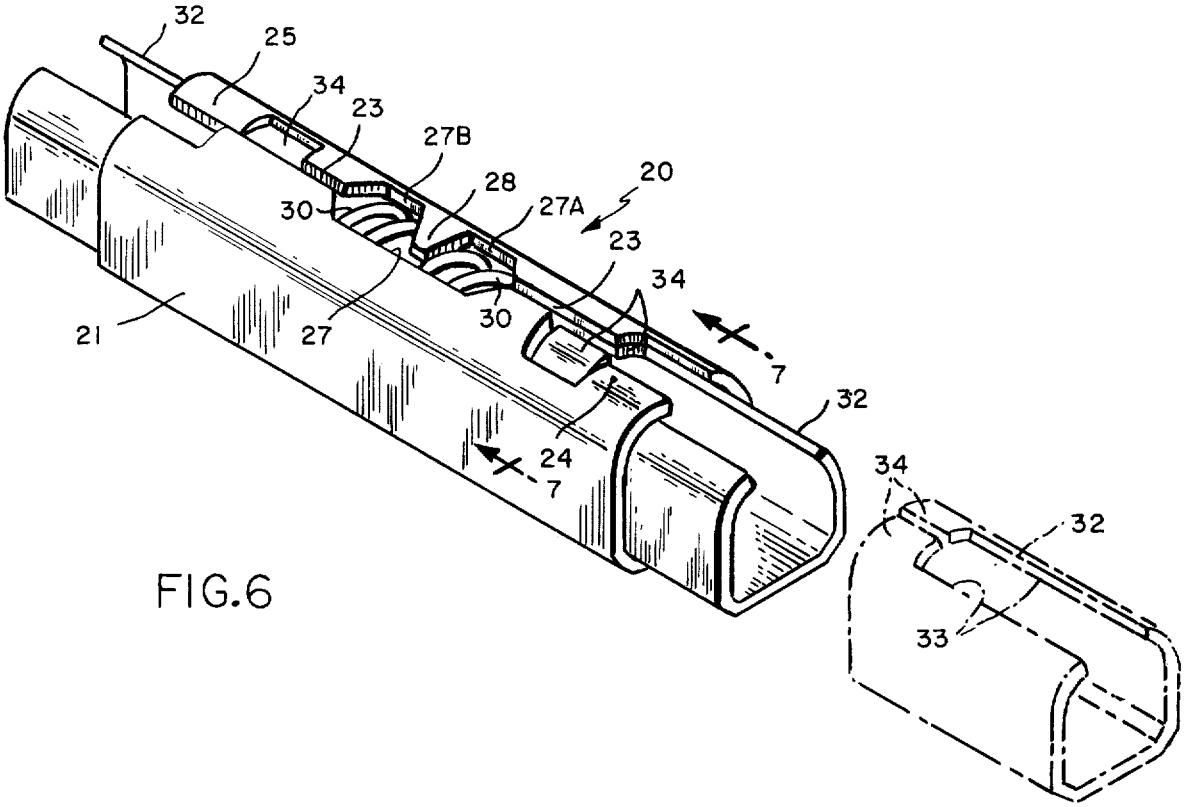
FIG. 6 is an enlarged perspective view looking at the bottom of an assembled self-contained component for an end connector with one of the inserts shown in dot dash at the right of the view.
Figure 7:
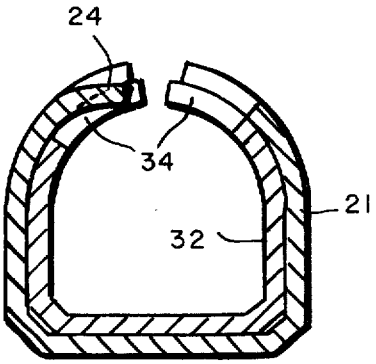
FIG. 7 is a section taken on the line 7—7 of FIG. 6.
Figure 8:
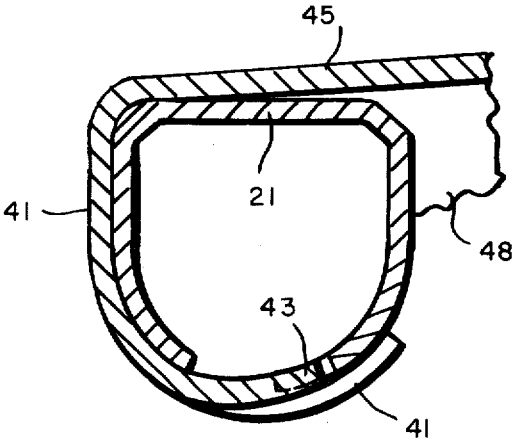
FIG. 8 is a section taken on the line 8—8 of FIG. 4.

The end attachment 14 of this invention comprises a self-contained component 20 (FIG. 6) which comprises a generally tubular member 21 formed from a strip of metal which is bent into tubular form to provide a longitudinal slit 23 between adjacent ends of the strip. A pair of tabs 24, 25 are formed from the strip of metal, one adjacent to one end of the strip and the other adjacent to the other end, the ends of these tabs being bendable towards the interior of the tubular member 21. It will be observed that the tab 24 extends in one direction near one end of the strip of metal and that tab 25 extends in the opposite direction adjacent to the other end of the strip. With this construction, the generally tubular member is symmetrical and automatic assembly of the self-contained component is facilitated. However, the component can be less easily assembled automatically if these tabs extend in the same direction and in use it functions as well as the preferred embodiment.

Oppositely positioned cutout portions 27 are provided substantially intermediate the ends of the generally tubular member 21 and a tab 28 extends inwardly from the side of one of these cutout portions thereby dividing it into a pair of cutout portions 27A and 27B, the function of which will be described below.

In the preferred embodiment, the self-contained component 20 also includes a pair of coiled compression springs 30 which slide loosely within the generally tubular member 21 and the inner ends of which engage the tab 28 which is bent inwardly of the tubular member 21 and forms stop means substantially midway between its ends. However, in its broad aspect, the invention contemplates use of a single coiled compression spring without stop means. In another embodiment, a single coiled compression spring may be used together with a tab such as the tab 28, the end of which is bent inwardly between a pair of coils of the spring to act as stop means to prevent longitudinal movement of the spring with respect to the generally tubular member 21.

The self-contained component 20 also includes a pair of generally tubular inserts 32 adapted to slide within the generally tubular member 21. Each insert is formed from a strip of metal and is provided with a generally rectangular slot 33 formed between the edges of the strip of metal, this slot having an open end and an inner end formed by the edges of the pair of tabs 34 which extend inwardly towards each other from the adjacent ends of the strip of metal.

Figure 5:
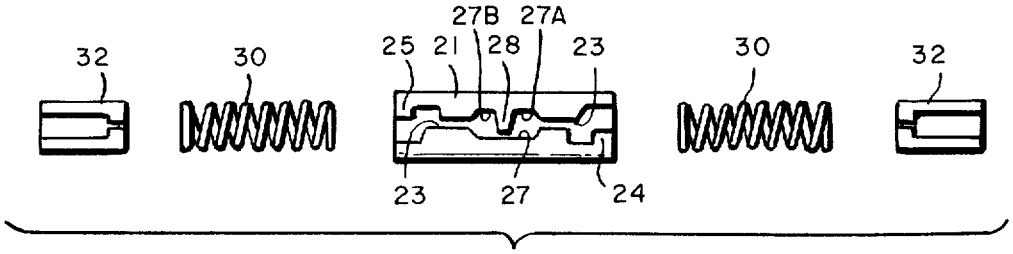
FIG. 5 is an exploded view looking at the bottom of the generally tubular member, pair of coiled compression springs and pair of generally tubular inserts in positions prior to assembly to form a self-contained component for an end connector.

In FIG. 5 the parts of the preferred self-contained component are shown in positions ready to be assembled. They can be assembled by an automatic machine which simultaneously inserts the springs 30 at opposite ends of the tubular member 21 until their ends abut the stop means 28, simultaneously inserts the inserts 32 at opposite ends of the generally tubular member 21 and moves them inwardly to compress the springs 30 until the inner ends of the rectangular slots 33 pass beyond the tabs 24 and 25 of the generally tubular member 21 and then the ends of these tabs are bent into the longitudinal slots 33. The pressure against the outer ends of the inserts 32 is then released whereupon the springs move the inserts outwardly and the inner edges of the tabs 24 and 25 engage the outer edges of the tabs 34, thereby stopping further outward movements of the inserts by the coiled springs.

The cost of making the self-contained components and of assembling them is extremely small and they are extremely durable.

The ornamental top shell 40 comprises a generally tubular portion 41 which surrounds at least the upper and end portions and a substantial part of the lower portion of the generally tubular member 21 of the self-contained component 20 and this top shell is provided with a pair of tabs 43 which are bent into the openings 27A and 27B of the generally tubular member 21 thereby to secure the top shell 40 to the self-contained component 20.

Figure 2:
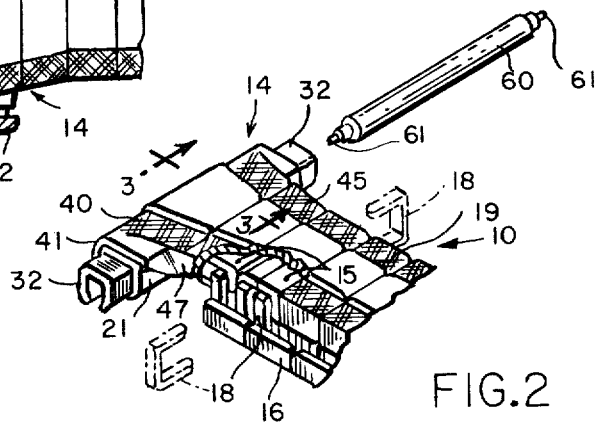
FIG. 2 is a perspective view of a spring bar of a wrist watch, an end connector embodying this invention and a watch band with parts of the watch band broken away and two of the link connecting means of the watch band shown in dot dash.
Figure 3:
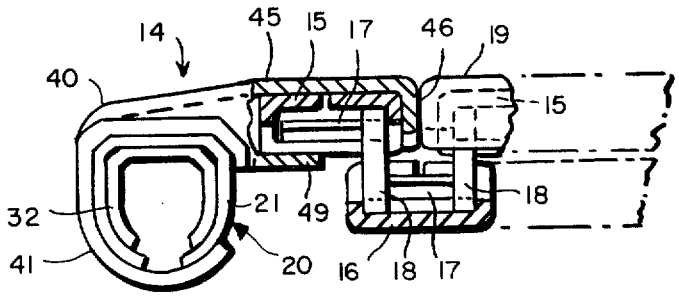
FIG. 3 is an enlarged section taken on the line 3—3 of FIG. 2.
Figure 4:
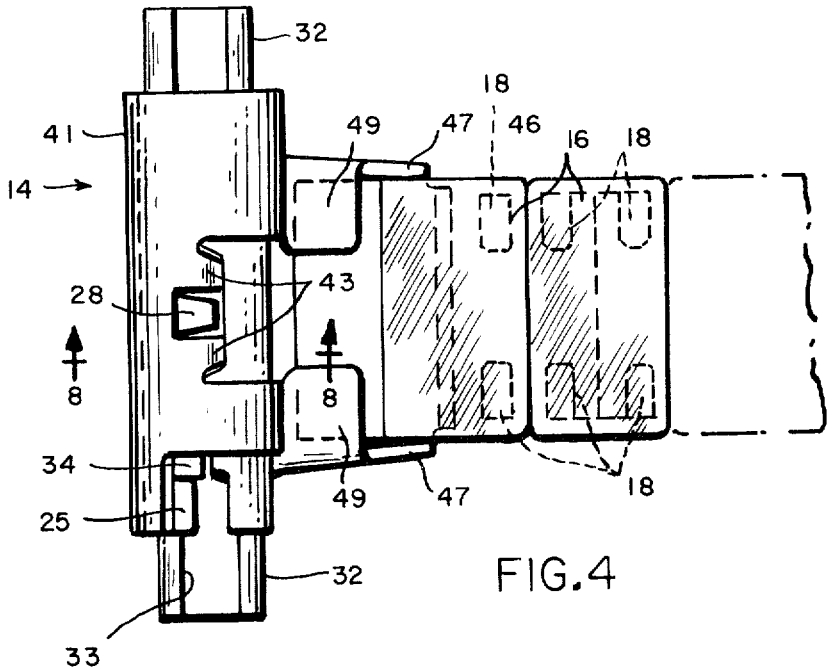
FIG. 4 is an enlarged bottom plan view of the end connector and watch band shown in FIG. 2.

The top shell 40 is provided with a member 45 which extends laterally from the generally tubular portion 41 as shown in FIGS. 2, 3 and 4. This member 45 is provided with a downwardly extending flange 46 which is positioned between the end top link 15 of the watch band and the top shell 19 of the adjacent link of the watch band. The laterally extending member 45 is also provided with downwardly extending flanges 47 which cover the ends of the end top link 15. The flanges 47 are provided with a pair of inwardly bent tabs 49 which engage the bottom wall of the end top link 15 of the watch band thereby cooperating with the flange 46 to secure the top shell 40 of the end link 15 to the watch band.

The generally tubular member 21 and the inserts 32 of the self-contained component may be made of stainless steel or other suitable metal. The top shell 40 may be made of gold-filled material or stainless steel or other suitable material.

It will be observed that the top shell 40 is impressed with the design of the top links of the watch band so that the design of the watch band is continuous from end to end thereof including the end connector. Because the inner surface of the generally tubular portion 41 of the top shell 40 is in contact with the outer surface of the generally tubular member 21 of the self-contained component a deeply impressed design which carries through the metal of the top shell may be impressed on the top shell without interfering with the free sliding movement of the inserts 32 which are only in contact with the inner surface of the generally tubular member 21.

In use the spring pin 60 of the watch is inserted through the inserts 32 and coiled springs 30, one of the pins 61 is inserted in one of the cavities 62 of a watch lug, then the inserts are slid inwardly of the tubular member 21 further compressing the springs and the other pin 61 is then inserted in the cavity of the other watch lug and released, thereby securing the spring pin between the lugs. The springs 30 urge the inserts outwardly so they abut the inner sides of the lugs and the end attachment is secured in place as shown in FIG. 1. They also centralize the end attachment between the lug 12 of the watch. When a single coiled spring is used instead of two springs and the tab 28 is bent inwardly between two coils of the spring, the end attachment is also centralized between the lugs of the watch by the tab and spring.

To remove the end connector, it is merely necessary to reverse the above steps.

Thus the end attachment may be used with watches in which the lugs are spaced different distances apart.

For men's watch bands a longer end attachment is provided.

End attachments embodying this invention may be used with snake chain and buckle secured watch bands and watch bands made of components of the type shown and described in copending application Ser. No. 386,069 filed by Rieth and Hoffman Aug. 6, 1973, now U.S. Pat. No. 3,844,136 dated Oct. 29, 1974. They may also be used with all types of expansion watch bands such as lazy tongs or X type watch bands and others which are well known to persons skilled in the art.

It will be apparent to persons skilled in the art that this invention has solved the above described long-felt need and satisfied the above described objects.

While one desirable embodiment of the invention has been shown in the drawings, it is to be understood that this disclosure is for the purpose of illustration only and various changes in shape, proportion and arrangement of parts as well as the substitution of equivalent elements from those shown and described herein may be made without departing from the spirit and scope of the invention as set forth in the appended claims.

I claim:

1. An end attachment for watch bands adapted to be mounted between spaced lugs of a wrist watch comprising a generally tubular member formed from a strip of metal, coiled compression spring means within said tubular member, a pair of generally tubular inserts adapted to slide within said generally tubular member, each insert being formed from a strip of metal and each insert having a generally rectangular slot formed between the edges of said strip which has an open end and an inner end formed by the edges of a pair of tabs which extend inwardly towards each other from the adjacent ends of said strip, a pair of tabs, one adjacent to one end of the strip from which said generally tubular member is formed and the other adjacent to the other end thereof, the ends of said tabs extending respectively into said rectangular slots and engaging the edges of said tabs of said inserts, thereby to stop outward movements of said inserts by said coiled spring means, and an ornamental top shell, said top shell comprising a generally tubular portion surrounding at least the upper and end portions and part of the lower portion of said generally tubular member, means for securing said generally tubular portion of said top shell to said generally tubular member, and a member extending laterally from the generally tubular portion of the top shell including means for attaching it to the end of a watch band.

2. An end attachment according to claim 1 wherein said generally tubular member, coiled compression spring means and pair of generally tubular inserts consist of a self-contained component and the generally tubular portion of the ornamental top shell is applied to the exterior of said generally tubular member.

3. An end attachment according to claim 1 wherein said ornamental top shell is impressed with the design of the links of the watch band to which the end attachment is to be attached, whereby the ornamental design impressed in said top shell does not interfere with the sliding movements of said inserts within said generally tubular member.

4. An end attachment according to claim 1 wherein said generally tubular member comprises stop means substantially midway between its ends for engaging said coiled compression spring means.

5. An end attachment according to claim 4 wherein said coiled compression spring means comprises a pair of coiled compression springs, one extending outwardly from one side of said stop means and the other extending outwardly from the other side thereof.

6. An end attachment according to claim 4 wherein the ends of said strip of metal from which said generally tubular member is formed comprise oppositely positioned cutout portions substantially intermediate its ends and said stop means comprises a tab extending from the side of one of said cutout portions thereby dividing said one cutout portion into a pair of cutout portions and said means for securing said generally tubular portion of said top shell to said generally tubular member comprises a pair of spaced tabs which extend into said pair of cutout portions.

7. An end attachment according to claim 1 wherein the tab adjacent to one end of the generally tubular member extends in one direction near one end of the strip of metal and the tab adjacent to the other end of the generally tubular member extends in the opposite direction near the other end of the strip of metal.

8. A self-contained component for making an end attachment for watch bands adapted to be mounted between spaced lugs of a wrist watch comprising a generally tubular member formed from a strip of metal, a pair of tabs, one adjacent to one end of said strip and the other adjacent to the other end thereof, the ends of said tabs being bendable towards the interior of said tubular member, coiled compression spring means within said tubular member, [ and ]

a pair of *hollow* generally tubular inserts adapted to slide within said generally tubular member, each insert being formed from a strip of metal and each insert having a generally rectangular slot formed between the edges of said strip which has an open end and an inner end formed by the edges of a pair of tabs which extend inwardly towards each other from the adjacent ends of said strip, *and*

*the outer surface of said self-contained component being devoid of any lateral projection,* whereby said component can be assembled by an automatic machine which inserts said coiled compression spring means into said tubular member and then simultaneously inserts said *hollow* inserts at opposite ends of said tubular member with the open ends of their rectangular slots pointing outwardly and moves them inwardly compressing said spring means until the inner ends of said rectangular slots pass beyond said tabs of the generally tubular member and then bends the ends of said tabs into said longitudinal slots, whereby the inner edges of said tabs of the generally tubular member engage the edges of said tabs which form the inner ends of the rectangular slots of the inserts, thereby to stop outward movements of said inserts by said coiled springs.

9. A component according to claim 8 wherein the tab adjacent to one end of the generally tubular member extends in one direction near one end of the strip of metal and the tab adjacent to the other end of the generally tubular member extends in the opposite direction near the other end of the strip of metal.

10. A component according to claim 8 which also comprises stop means extending inwardly from said generally tubular member substantially midway between its ends for engaging said coiled compression spring means.

11. A component according to claim 10 wherein said coiled compression spring means comprises a pair of coiled compression springs, one extending outwardly from one side of said stop means and the other extending outwardly from the other side thereof.

12. A component according to claim 10 wherein said stop means comprises a tab extending from one end of said strip of metal substantially midway between its ends.

13. A component according to claim 10 wherein the ends of said strip of metal from which said generally tubular member is formed comprise oppositely positioned cutout portions substantially midway between their ends and said stop means comprises a tab extending from one side of one of said cutout portions substantially intermediate its ends thereby dividing said one cutout portion into a pair of cutout portions.

* * * * *